US009759558B2

(12) United States Patent
Altini (10) Patent No.: US 9,759,558 B2
(45) Date of Patent: Sep. 12, 2017

(54) DEVICE AND METHOD FOR AUTOMATICALLY NORMALIZING THE PHYSIOLOGICAL SIGNALS OF A LIVING BEING

(71) Applicant: Stichting IMEC Nederland, Eindhoven (NL)

(72) Inventor: Marco Altini, Eindhoven (NL)

(73) Assignee: Stichting IMEC Nederland, Eindhoven (NL)

( * ) Notice: Subject to any disclaimer, the term of this patent is extended or adjusted under 35 U.S.C. 154(b) by 220 days.

(21) Appl. No.: 14/471,158

(22) Filed: Aug. 28, 2014

(65) Prior Publication Data
US 2015/0073720 A1    Mar. 12, 2015

(30) Foreign Application Priority Data

Sep. 6, 2013    (EP) .................................... 13183288

(51) Int. Cl.
| | | |
|---|---|---|
| G01N 33/48 | (2006.01) | |
| G01N 33/50 | (2006.01) | |
| G01B 21/00 | (2006.01) | |
| A61B 5/0205 | (2006.01) | |
| A61B 5/11 | (2006.01) | |
| A61B 5/16 | (2006.01) | |
| A61B 5/00 | (2006.01) | |
| G06F 17/10 | (2006.01) | |
| G06F 19/12 | (2011.01) | |
| G01C 22/00 | (2006.01) | |
| A61B 5/024 | (2006.01) | |
| A61B 5/08 | (2006.01) | |
| A61B 5/053 | (2006.01) | |

(52) U.S. Cl.
CPC ............ *G01B 21/00* (2013.01); *A61B 5/0205* (2013.01); *A61B 5/1112* (2013.01); *A61B 5/1118* (2013.01); *A61B 5/1123* (2013.01); *A61B 5/165* (2013.01); *A61B 5/4866* (2013.01); *A61B 5/6802* (2013.01); *G01C 22/00* (2013.01); *G01C 22/006* (2013.01); *G06F 17/10* (2013.01); *G06F 19/12* (2013.01); *A61B 5/0002* (2013.01); *A61B 5/02055* (2013.01); *A61B 5/02438* (2013.01); *A61B 5/0533* (2013.01); *A61B 5/0816* (2013.01); *A61B 2560/0223* (2013.01)

(58) Field of Classification Search
None
See application file for complete search history.

(56) References Cited

U.S. PATENT DOCUMENTS

| | | | |
|---|---|---|---|
| 5,976,083 A | 11/1999 | Richardson et al. | |
| 2009/0150178 A1* | 6/2009 | Sutton .................... | G07C 1/22 705/2 |

FOREIGN PATENT DOCUMENTS

| | | |
|---|---|---|
| WO | 2010/025467 A1 | 3/2010 |
| WO | WO 2012/054555 A2 * | 4/2012 |

OTHER PUBLICATIONS

Altini et al., "Energy Expenditure Estimation Using Wearable Sensors: A New Methodology for Activity-Specific Models," Wireless Health, Nov. 2012.
Brage et al., "Branched equation modeling of simultaneous accelerometry and heart rate monitoring improves estimate of directly measured physical activity energy expenditure," Journal of Applied Physiology, 96(1):343-351, Aug. 2003.
Brage et al., "Hierarchy of individual calibration levels for heart rate and accelerometry to measure physical activity," J. Appl. Physiol. vol. 103, pp. 682-992, 2007.
Wijsman et al., "Towards Mental Stress Detection Using Wearable Physiological Sensors," IEEE EMBS 2011, pp. 1798-1801, 2011.
Extended European Search Report from a related international patent application, serial No. EP 14 18 0263 dated Jan. 20, 2015.
"Palms: Personal Activity Location Measurement System—Temporal/Spatial Analysis of Personal Sensor Data", developed by UCSD under NIH/NCI, featured in Feb. 16, 2011 issue of Nature on Measuring the Human "Exposome", 2 pages.
Brosh, A. et al., "Energy Cost of Cows Grazing Activity: Use of the Heart Rate Method and the Global Positioning System for Direct Field Estimation", Journal of Animal Science, vol. 84, Feb. 2, 2006, pp. 1951-1967.

* cited by examiner

*Primary Examiner* — Russell S Negin
(74) *Attorney, Agent, or Firm* — McDonnell Boehnen Hulbert & Berghoff LLP (57) ABSTRACT

An example device includes: a data input module configured to receive information about a living being's physiological signals, coordinates, and motion intensity; an activity recognition module configured to calculate, from information received about the living being's motion intensity, a living being's activity; a location recognition module, configured to calculate, from information received about the living being's coordinates, a living being's location; a memory storage configured to store information about the living being's physiological signals and activity in association with the location; a normalization parameters estimator module configured to use a mathematical model to calculate a plurality of normalization parameters for a plurality of detected activities and locations; and a model selector module configured to determine, based on the plurality of normalization parameters and the living being's location, a set of location-specific normalization parameters used to further calculate normalized physiological signals for the living being.

16 Claims, 5 Drawing Sheets

DEVICE AND METHOD FOR AUTOMATICALLY NORMALIZING THE PHYSIOLOGICAL SIGNALS OF A LIVING BEING

CROSS-REFERENCE TO RELATED APPLICATIONS

This application claims priority to European Patent Application Serial No. 13183288.3 filed Sep. 6, 2013, the contents of which are hereby incorporated by reference in their entirety.

FIELD OF THE INVENTION

The present disclosure is related to devices and methods for automatically normalizing physiological signals of a living being and calculating further living being's relevant information derived from said normalized physiological signals.

BACKGROUND

Many self-monitoring applications today rely on wearable sensors combining inertial (e.g. accelerometer, gyroscope) and physiological (e.g. heart rate, galvanic skin response, skin temperature, respiration) data to develop accurate algorithms. These applications span from physical (e.g. activity type, energy expenditure estimation, fitness estimation) to mental health (e.g. stress, meditation). It has been also noted that better results are reported, for both physical and mental health, when physiological signals (and not only inertial data) are used. However, some main challenges affect state of the art biomedical data analytics. For example, physiological signals differ greatly between individuals and/or change over time due to different factors (people's health, age, etc.). Therefore biomedical data analytics shall take into account not only changes between people, but also changes within an individual over time. When data is not normalized, high error between individuals is reported compared to when data is normalized or individually calibrated.

In the document "Towards Mental Stress Detection Using Wearable Physiological Sensors," by J. Wijsman et al., IEEE EMBS, pp. 1798-1801, 2011, data is normalized as part of the feature extraction/preparation procedure, before its use as input for the algorithms. This is done applying standard normalization techniques (e.g. remove mean and divide by standard deviation, or divide by range, etc.). However, the procedure is not extendable to new subjects, and for which there is a need to perform the complete protocol again.

In the document "Branched equation modeling of simultaneous accelerometry and heart rate monitoring improves estimate of directly measured physical activity energy expenditure," by S. Brage, Journal of Applied Physiology, 96(1): 343-351, August 2003, data is normalized with respect to a baseline. However, physiological signals do not differ only in offset with respect to a baseline, but also in ranges.

In the document "Hierarchy of individual calibration levels for heart rate and accelerometry to measure physical activity," by S. Brage et al., J Appl Physiol, 2007, data is normalized during specific protocols, that is, it requires individual calibration. However, calibration needs to be performed using sometimes expensive equipment (e.g. indirect calorimetry for energy expenditure), or requires to be performed very often due to changes in physiological signals over time (e.g. changes in fitness level or age).

SUMMARY

According to an embodiment, there is provided an improved device and method for calculating normalized physiological signals of a living being (e.g. human or animal). Advantageously, the proposed device and method can provide more accurate results at an individual level, e.g. reducing inter-individual variability. Additionally, according to an embodiment, the device and method may advantageously take into consideration differences in physiology signals due to environmental factors, for example, by using a different model based on location information of the living being, and thus reducing differences within individuals due to environmental conditions. Additionally, according to an embodiment, the device and method herein described is capable also of calculating other living being's relevant information derived from said normalized physiological signals, such as for example an energy expenditure level or a stress level of a living being.

According to an exemplary embodiment, there is provided a device comprising: a data input module configured to receive information about the living being's physiological signals, coordinates, and motion intensity; an activity recognition module configured to calculate, from information received about the living being's motion intensity, a living being's activity; a location recognition module, configured to calculate, from information received about the living being's coordinates, a living being's location; a memory storage to store information about said living being's physiological signals and said activities associated with said location; a normalization parameters estimator module configured to calculate, from a plurality of physiological signal values associated with each detected activity and location, statistics of the distribution of the physiological signals values for each activity or a subset of activities and use a mathematical model to calculate a plurality of normalization parameters, depending on the location information; and a model selector module configured to determine, from the plurality of normalization parameters and location information, a set of location-specific normalization parameters used to further calculate normalized physiological signals.

Advantageously, according to an exemplary embodiment of the invention, the device is able to calculate the normalization parameters (range and baseline) of the living being's physiological signals, such as a human or animal, without the need to perform a specific exercise test. Additionally, the device according to an exemplary embodiment of the invention is able to use the living being's location in order to determine different normalization parameters based on the user location. This is advantageous since physiological signals may change within a person due to environmental effects (e.g. temperature, higher stress at work, etc.) and different normalization parameters based on location can take these effects into account, providing better physiological signal normalization in the short term (e.g. during a day). Additionally, the device according to an exemplary embodiment of the invention is able to continuously and automatically recalculate the normalization parameters of the living being over time, by gathering data about the living being's activities, locations and physiological signals values, so that the normalization parameters values are updated avoiding the need to perform further exercise tests. This is advantageous since the device according to an embodiment of the invention is able to normalize the physiological signals during the lifetime of a living being in a non-invasively manner and seamlessly integrated without affecting the daily normal activities of the living being. This is further advantageous since the physiological signals may change over time within an individual due to for example age, and the automatic normalization is able to take this into account by using data continuously collected during activities of daily living for a period of time.

The living being may be a human or an animal. The anthropometric characteristics may comprise one or more of a gender, BMI, height, age, and weight of the living being.

According to an embodiment, the device performs activity recognition from the received living being's motion intensity information and associates those activities to the physiological signals values of the subject when performing those activities. Advantageously said activities are different activities of daily living.

According to an embodiment, the activity recognition module is configured to determine at least a rest activity and a moving activity of the living being. According to an embodiment, the activity recognition module may also manage storage of physiological signal values associated with each of said determined activities, and storage of the motion intensity associated to the moving activity.

According to an embodiment, the device performs location recognition from the received living being's coordinates information and associates those locations to the activities and physiological signals values of the subject in these locations. Advantageously said locations are different places, for example, home or office. Then, the device according to an embodiment of the invention uses the physiological signals information from the living being at different workloads (activities) and locations and calculates the normalization parameters (baseline and range) values for each location.

According to an embodiment, the location recognition module is configured to determine at least two different locations. According to an embodiment, the location recognition module may also manage storage of physiological signal values associated with each of said determined locations.

According to an embodiment, the location recognition and storage module may be configured to detect three different locations, namely "at home", "at work" and "out", and may also store physiological signals values and detected activities and motion intensities associated with each location.

According to another embodiment, the information about physiological signals may be information about the living being's heart rate, or galvanic skin response, or respiration, or other physiological signals measured using non-invasive wearable sensors.

According to another embodiment, the information about motion intensity may be information about the body's acceleration and/or motion speed. According to another embodiment, the information about motion intensity may be information about the body's acceleration and the device further comprises motion calculation means configured to calculate, from said information about the body's acceleration, the living being's motion speed. According to another embodiment, the information about motion intensity may be information about the body's acceleration and the device further comprises location positioning means configured to calculate the living being's motion speed.

According to another embodiment, the information about coordinates may be information about the body's latitude and longitude. According to another embodiment, the information about coordinates may be information about the living being latitude and longitude and the device further comprises location calculation means configured to determine, from said information about the coordinates, the living being's location.

According to still another embodiment, the moving activity is associated to at least a first motion intensity and the normalization parameters estimator module is configured to calculate, for each location, a first physiological signal values summary from the physiological signal values distribution associated to the first motion intensity and a second physiological signal summary from the physiological signal value distribution associated to the rest activity.

According to still another embodiment, the normalization parameters estimator module is configured to calculate statistics of the physiological signals values distribution associated to a detected activity and motion intensity for a specific location, in order to store summarized physiological signals information for each activity or a subset of activities in a given location. For example, the normalization parameters estimator module may calculate the mean or the median of the physiological signals values distribution associated to a detected activity and motion intensity in a given location, so that from a plurality of physiological signal values associated to a detected activity and motion intensity in a given location, the normalization parameters estimator module summarizes that plurality of values in one or more physiological signal values for each location.

According to an embodiment, the normalization parameters estimation module uses a mathematical model based on information about physiological signals values distribution, activity and location.

According to an embodiment, the mathematical model expresses the relation between a plurality of physiological signal values associated with each detected activity and location, and the baseline and range (the normalization parameters) of such physiological signals for a living being. The mathematical model may further consider information about the anthropometric characteristics of the living being.

According to still another embodiment, the mathematical model expresses the relation between the summarized physiological signals values, the associated detected activity or subset of activities, the associated motion intensity, the anthropometric characteristics and the normalization parameters (baseline and range) of the specific physiological signal for a living being.

According to an embodiment, the model selector module is configured to calculate normalized physiological signals by selecting the normalization parameters (baseline and range) of the physiological signals estimated by the mathematical model used by the normalization parameters estimation module, and applying the location-specific normalization parameters to the physiological signals, depending on the living being location.

According to an embodiment, the device further comprises an application module configured to calculate, from the living being's normalized physiological signals, an additional application-specific parameter associated to the living being. Optionally, the application module may also use motion intensity, coordinates, and/or anthropometric characteristics for such calculation. Said additional application-specific parameter may be, for example, an energy expenditure or an stress level indication of a living being. Advantageously, the device is able to accurately determine the energy expenditure level or the stress level of a living being.

According to another embodiment, the application module may use a mathematical model based on information about physiological signals normalization parameters, physiological signals, acceleration, location, anthropometric characteristics and reference depending on the application type, for example, VO2 reference from indirect calorimetry in case of energy expenditure or cortisol level for stress. Examples of such mathematical model may be multiple linear regression models. The coefficients of the multiple linear regression models may be derived using information about activity performed, physiological signals distribution, acceleration, location, anthropometric characteristics and reference depending on the application, from a number of living beings, e.g. humans, performing a range of different activities.

Advantageously, the device for monitoring the additional application-specific parameter of a living being according to an embodiment of the invention, further uses the information about the living being's normalized physiological signals to calculate the additional parameter, and thereby improving the accuracy of the additional parameter estimation, provided for that living being. The device according to an embodiment of the invention advantageously improves the accuracy of the estimation reducing inter-individual error by using automatically normalized physiological signals, derived during activities of daily living. The device according to an embodiment of the invention advantageously improves the accuracy of the estimation reducing within-individual error by using different automatically normalized physiological signals depending on the living being location.

According to an embodiment, the device is configured to receive information from sensors directly connected to the device or further comprising a wireless transmission module which receives information from sensors located in the living being.

The invention also relates to a system comprising a device according to any of the embodiments herein described, and to a method for calculating at least one parameter of a living being, the method comprising: receiving information about the living being's physiological signals, motion intensity and location; detecting the living being's activity from information received about the living being's motion intensity and storing information about said living being's physiological signals and said motion intensity associated with that detected activity; detecting the living being's location from information received about the living being's coordinates and storing information about said living being's physiological signals and said coordinates associated with the detected activity and location; determining, from a plurality of physiological signals values associated with each detected activity, statistics of the distribution of physiological signals values for each activity or a subset of activities and in each location; calculating, using the information from the normalization parameters estimator module, optionally the anthropometric characteristics, the baseline and range of said physiological signals in each location; and normalizing, using the baseline and range of said physiological signals in each location the physiological signals of the living being the current living being's location. The method may further comprise calculating, from the living being's normalized physiological signals, an additional application-specific parameter associated to the living being.

BRIEF DESCRIPTION OF THE FIGURES

The above and other aspects of the invention will be apparent from the following description and with reference to the non-restrictive example embodiment(s) described hereinafter.

DETAILED DESCRIPTION

Figure 1:
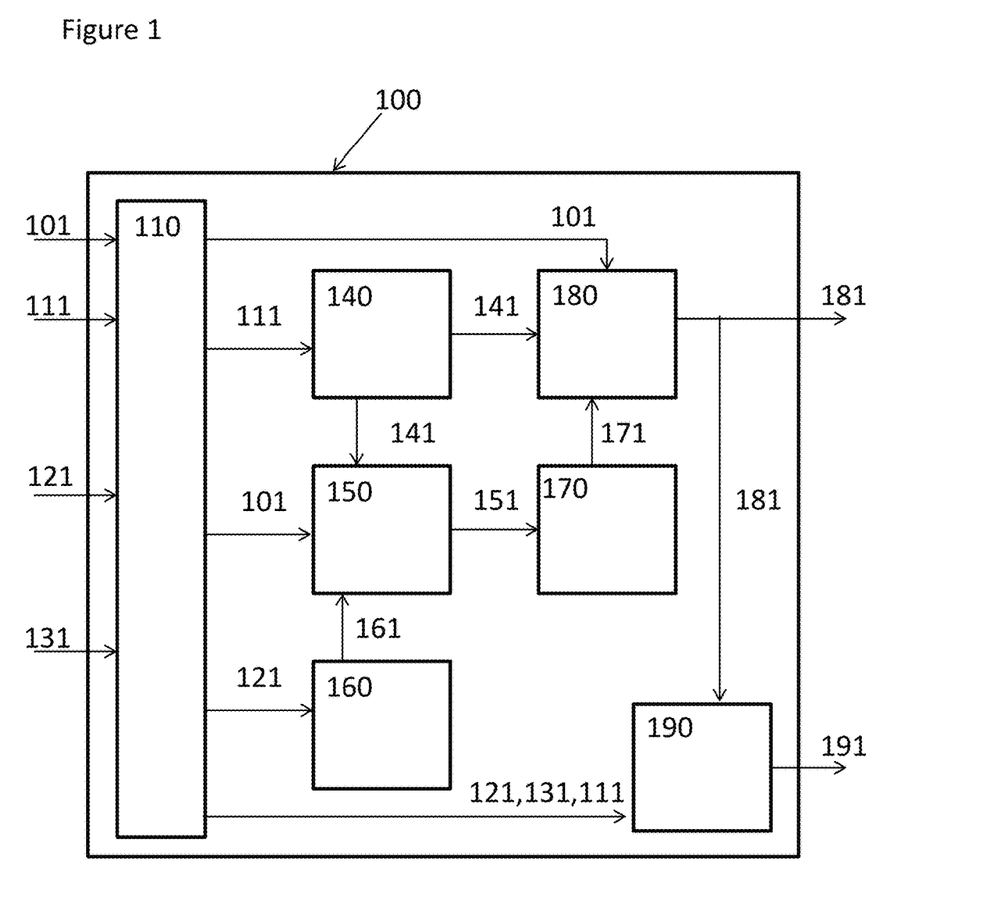
FIG. 1 shows a block diagram of an exemplary embodiment of a device according to the invention.

FIG. 1 shows a first block diagram of an exemplary embodiment of a device 100 according to the invention, comprising a data input module 110 which receives information about the living being's physiological signals 101 (such as, for example, the living being's heart rate value, galvanic skin response level value, respiration value, etc.), motion intensity 121, coordinates 111, and anthropometric characteristics 131; an activity recognition module 160, which determines, calculates or detects, from information received about the living being's motion intensity 121, the living being's different activities 161; a location recognition module 140, which determines, calculates or detects, from information received about the living being's coordinates 111, the living being's different locations 141; a memory storage 150 where to store information about the living being's physiological signals 101 and motion intensity 121 associated with each of the detected activities 161 and information about the living being's physiological signals 101 and coordinates 111 associated with each of the determined locations 141; a normalization parameters estimator module 170, which determines, calculates or detects, from the information about the living being's physiological signals 101 associated with each determined activity 161, and in each determined location 141, statistics of the distribution of the physiological signals values for each activity or a subset of activities, and determine a plurality of normalization parameters 171, e.g. a baseline and range of each physiological signal, in each location, using a mathematical model; a model selector module 180 which, according to an embodiment, uses the normalization parameters 171 together with the determined location 141, and optionally physiological signals 101, to calculate or derive a set of normalization parameters to be used (location-specific normalization parameters), to further calculate normalized physiological signals 181 based on the location information. The device may further comprise an application module 190, which determines or calculates, using the information from the calculated normalized physiological signals 181, an additional application-specific parameter 191 (e.g. energy expenditure or stress level) associated to the living being. The device may also receive information about the anthropometric characteristics 131 of the living being and use this information for calculating normalized physiological signals 181 and eventually the additional application-specific parameter 191.

Information about the living being's physiological signals 101 can be received from a heart beat rate (HR) or electrocardiogram (ECG) sensor in case of heart rate, from a wrist or arm-band in case of galvanic skin response (GSR), or generally speaking a body patch able to acquire information about, for example, ECG, HR, GSR, skin temperature, skin humidity, respiration or other physiological signal and may be information about current or real-time value of one or more of the above mentioned physiological signals for the subject.

According to one embodiment, the information about the living being's motion intensity 121 may be information about the living being body's acceleration and/or motion speed. This information may be provided, for example by an accelerometer sensor and/or by a global positioning system (GPS) device connected or sending information to the device 100. According to another embodiment, the information about motion intensity 121 may be information about the body's acceleration and the device 100 further comprises motion calculation means which calculate, from said information about the body's acceleration or from a GPS device, the living being's motion speed.

According to one embodiment, the information about the living being's coordinates 111 may be information about the living being's body latitude and longitude. This information may be provided, for example by GPS device connected or sending information to the device 100 or a mobile phone connected or sending information to the device 100 or a Wi-Fi or GSM module connected or sending information to the device 100. According to another embodiment, the information about the coordinates 111 may be information identifying and/or received from a wireless cell transmitter (e.g. a Wi-Fi transmitter) and the device 100 is able to determine the living being's location, such as for example "at work" or "at home" or "out", by identifying the presence or absence of such wireless cell transmitter. The location may be a current location for real-time calculations.

According to another embodiment, information about the anthropometric characteristics 131 of the living being can be information received from an input user interface or from another device about or related to, for example, the type, gender, body-mass index (BMI), height, age and/or weight of the living being.

It is also understood that the device 100 can receive all information needed for its functions from sensors or interface units directly connected to the device or via a wireless transmission module which receives information from sensors located in different locations of the living being. Therefore, the device 100 may be attached to the living being's body or separated from it, for example, implemented in a separate mobile unit or integrated in a mobile phone.

According to an embodiment, the activity recognition module 160 is able to determine, calculate or detect at least a "rest" activity and a "moving" activity of the living being, and manage the storage of physiological signal values 101 associated with each of the detected activities, and the motion intensity 121 associated to the "moving" activity. A rest activity can be for example lying down while sleeping or sitting at the desk while working, and a moving activity can be for example a normal activity of daily living such as walking Both activities can be recognized, for example, by using pattern recognition techniques applied on the accelerometer data.

According to an embodiment, the location recognition module 140 is able to determine, calculate or detect at least two locations, for example a "home" location and a "work" location, and manage the storage of physiological signal values 101 associated with each of the detected locations. According to an exemplary embodiment, locations can be pre-configured by the user providing as input the address where he or she lives and/or works, such address will be used to automatically retrieve the coordinates and use them to determine the user location when the application is running.

According to an embodiment, the normalization parameters estimation module 170 is configured to calculate statistics of the physiological signals values distribution associated to a detected activity and location and to the motion intensity of a detected activity. For example, according to an exemplary embodiment, the "moving" activity is associated to at least a first motion intensity and the normalization parameters estimation module 170 determines, for each detected location, a first physiological signal values summary from the physiological signal values distribution associated to the first motion intensity and a second physiological signal values summary from the physiological signal value distribution associated to the "rest" activity. According to another exemplary embodiment, the "moving" activity is associated to a first and a second motion intensity and the normalization parameters estimation module 170 determines, for each detected location, a first physiological signal values summary from the physiological signal values distribution associated to the first motion intensity and a second physiological signal values summary from the physiological signal value distribution associated to the second motion intensity. According to an exemplary embodiment, a physiological signal values summary of the physiological signal values distribution can be for example the calculation of the mean of the physiological signal value distribution for an activity or subset of activities in a specific location. According to an embodiment, with such first and second physiological signal values summary, the normalization parameters estimation module 170 calculates, using a certain mathematical model, a plurality of normalization parameters 171 (i.e. a baseline and range of the physiological signals) for each activity or a subset of activities and location. According to an exemplary embodiment, a first motion intensity may be, for example, walking at slow speed (e.g. 3 km/h), while a first physiological signal values summary from the physiological signal values distribution associated to the first motion intensity can be the median of the physiological signals values while walking at such speed. A second motion intensity may be, for example, walking at another speed (e.g. 4 km/h), while a second physiological signal values summary from the physiological signal values distribution associated to the second motion intensity can be the median of the physiological signals values while walking at such speed.

Examples of mathematical models used by the normalization parameters estimation module 170 for calculating the plurality of normalization parameters 171 are, for example, multiple linear regression models. The coefficients of the multiple linear regression models can be derived, for example, using information about activity performed, physiological signal distribution, acceleration, coordinates, anthropometric characteristics and/or measured baseline and range in different environments and while a number of human beings is performing a range of activities. The same could be applied for models related to animal beings.

According to an embodiment, the model selector module 180 is configured to calculate normalized physiological signals 181 by selecting the baseline and range of the physiological signals estimated by the mathematical model used in the normalization parameters estimation module 170, and removing the baseline from the physiological signal 101 as well as dividing the physiological signal by the range. An example of normalized physiological signal can be for example the heart rate of a human being, after removing the baseline and dividing by the range associated with a specific location.

Figure 2:
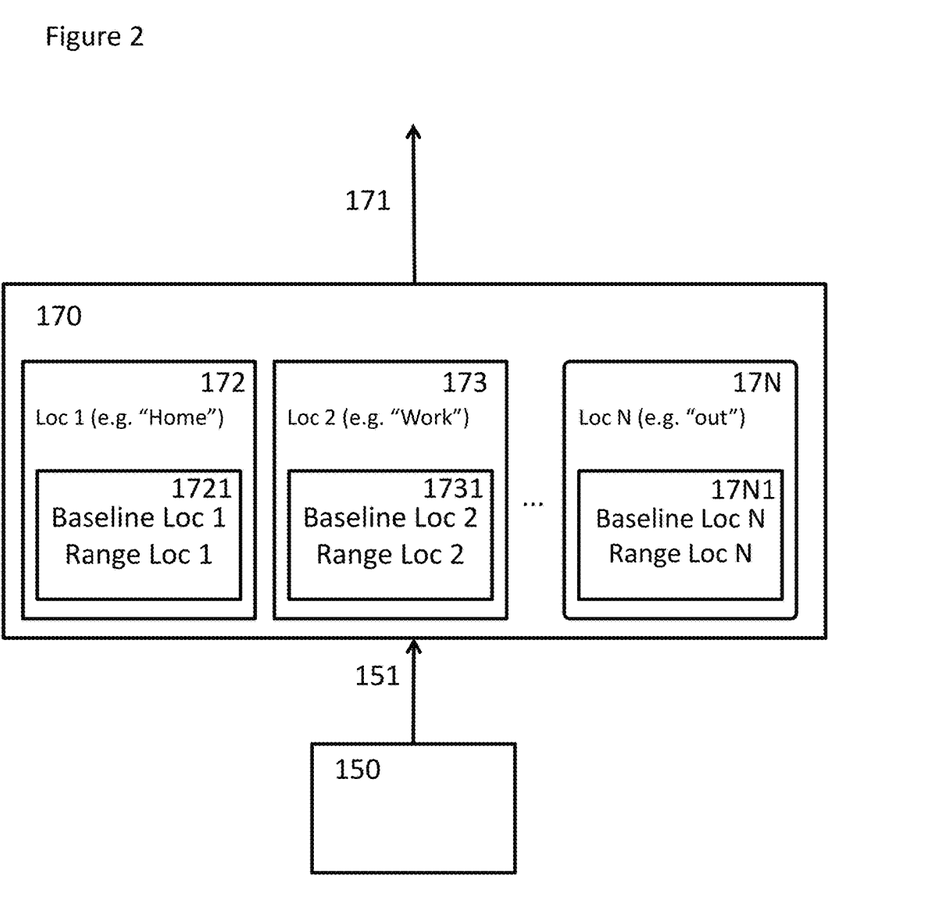
FIG. 2 shows a block diagram of an exemplary embodiment of a normalization parameters estimator module in a device according to the invention.

FIG. 2 shows a block diagram of an exemplary embodiment of a normalization parameters estimator module 170 in a device according to the invention. According to an embodiment, the normalization parameters estimator module 170 calculates statistics of the physiological signals distribution associated to a detected activity 161, motion intensity 121 and location 141 in order to store summarized physiological signals information, such as the baseline and range of the physiological signals in a particular location 171. According to the exemplary embodiment shown in FIG. 2, the baseline and range values 1721, 1731, 17N1, while in different locations 172, 173, 17N are determined by the normalization parameter estimator module using data stored in the memory storage 150. Data 151 received from the memory includes physiological signal values during activities of daily living such as "rest" and "walking", and is used in a mathematical model to derive a baseline and range in different locations. It shall be also understood that the memory storage 150 may comprise memory units located in different internal parts of the device and/or externally attached to it.

According to an embodiment, the mathematical model expresses the relation between the summary of physiological signal values, the associated detected activity or subset of activities 161, the associated motion intensity 121, the associated location 141, the anthropometric characteristics 131 and the normalized physiological signals 181 for a living being.

Figure 3:
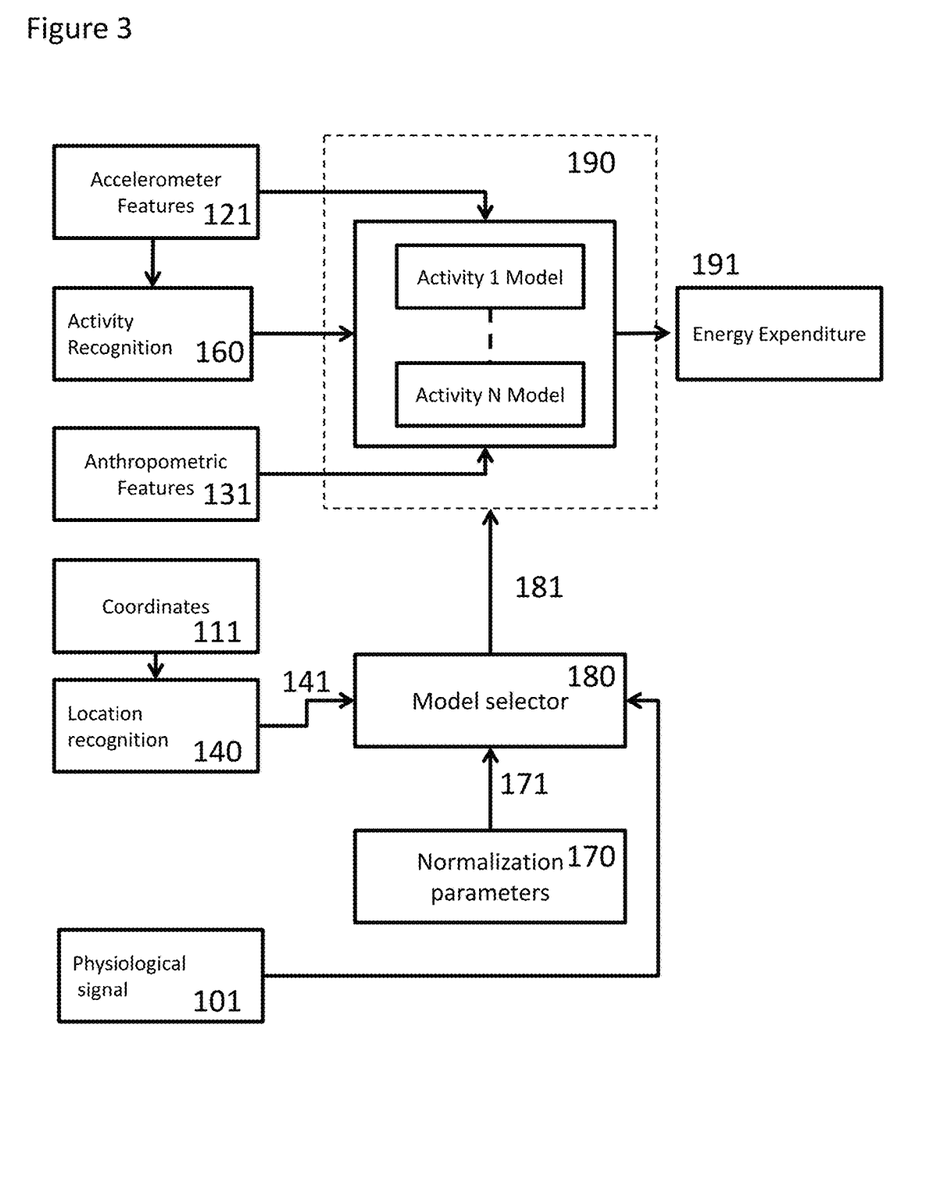
FIG. 3 shows a block diagram of another exemplary embodiment of a device according to the invention.

FIG. 3 shows a second block diagram of another exemplary embodiment of a device 100 comprising the same elements as the device shown in FIG. 1 and wherein the application module 190 is an energy expenditure module which calculates an energy expenditure 191 of a living being using the living being's normalized physiological signals 181, detected activity 161, motion intensity 121, location 141, physiological signals values 101 and any of the anthropometric characteristics 131.

State of the art energy expenditure estimation algorithms calculate energy expenditure in two steps: first, an activity is recognized by using the activity recognition module; the activity recognition module uses motion information from a motion module (e.g. accelerometer) to derive the activity performed by a human being; and secondly, an activity-specific energy expenditure model is applied to derive energy expenditure. An activity-specific energy expenditure model can be a multiple linear regression model (or a non-linear model) developed using motion information, physiological signals information, anthropometric characteristics and reference VO2 from a number of human beings performing the specific activity. A different model is used for each detected activity in order to capture the peculiar relation between an activity and energy expenditure. An example of such procedure is illustrated in FIG. 3. More details on this approach can be found in paper "*Energy Expenditure Estimation Using Wearable Sensors: A New Methodology for Activity-Specific Models,*" by Altini M. et al., Wireless Health, November 2012.

Figure 4:
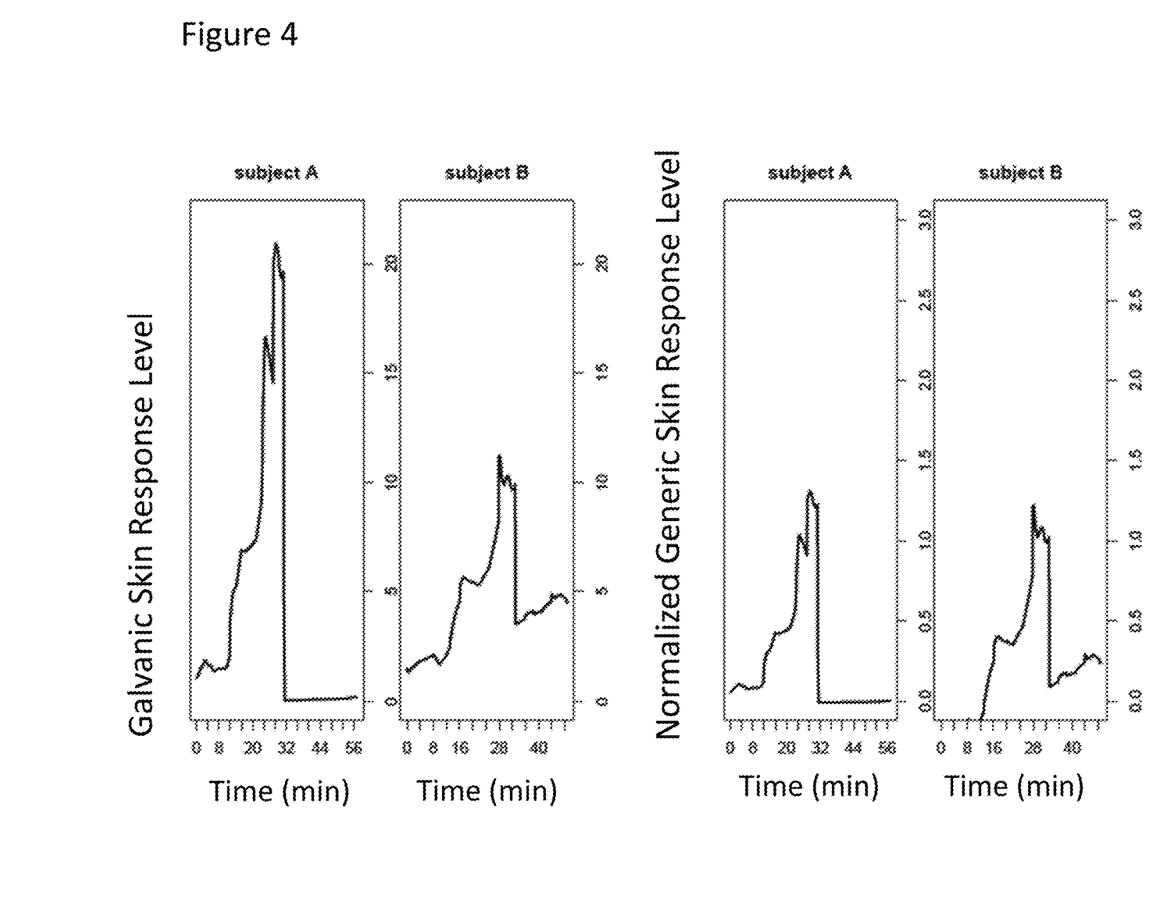
FIG. 4 illustrates an exemplary relation of Galvanic Skin Response (GSR) during various activities and the effect of the location dependent normalization, according to the invention.
Figure 5:
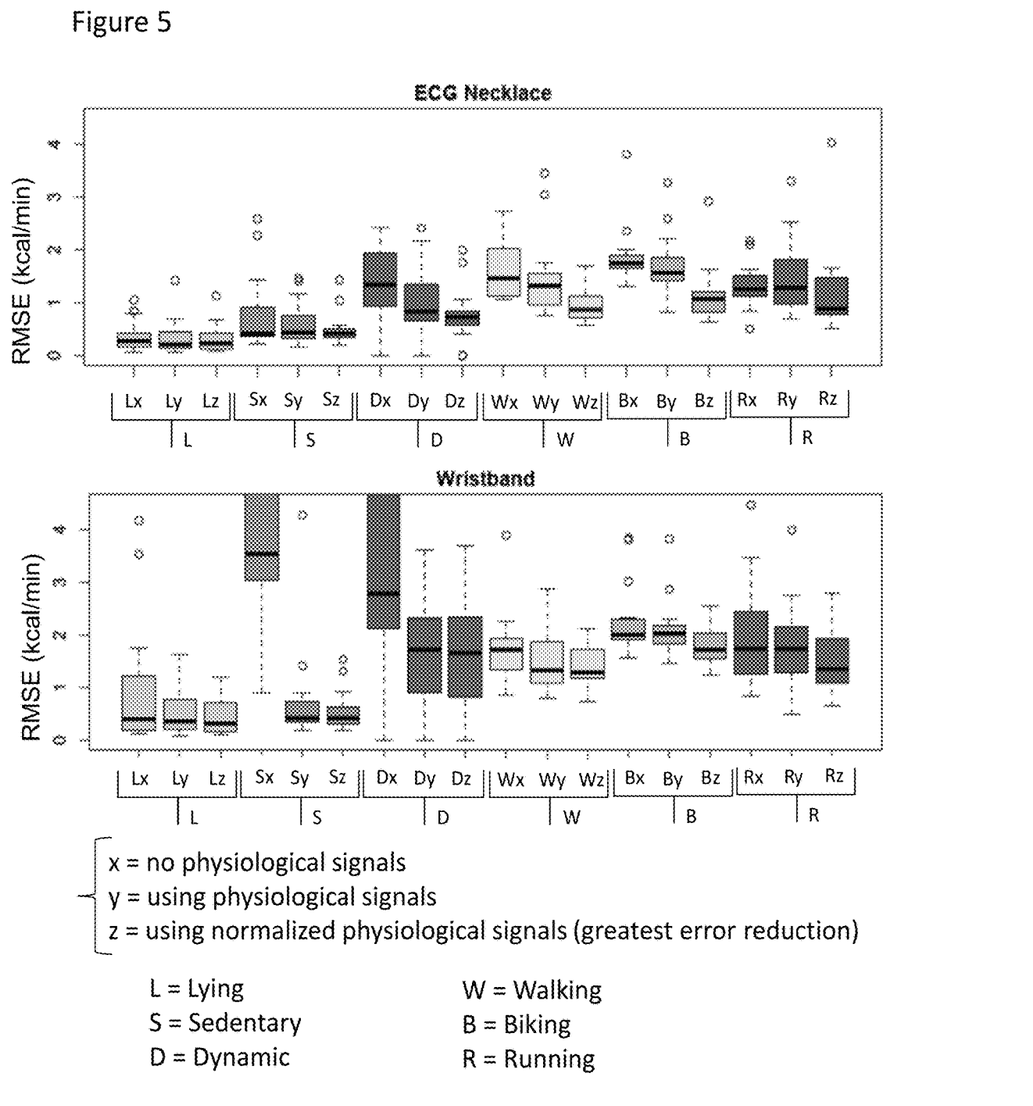
FIG. 5 shows results provided by exemplary energy expenditure algorithms in terms of error reduction when using a device according to an embodiment of the invention.

According to an embodiment of the present invention, energy expenditure can be estimated using the normalized physiological signals values in each different location, thus significantly reducing the error by taking into account that physiological signals varies largely between individuals and for the same individual in different environments, due to differences in physiology and environmental factors, as shown in FIG. 4 and FIG. 5.

It shall be noted that other applications can be envisaged which may use the living being's normalized physiological signals 181 and physiological signals 101 to calculate another application-specific parameter 191 associated to the living being. For example, according to another embodiment, the application module 190 may be a stress level module which calculates a stress level indication of a living being.

The functions of the modules described in FIGS. 1 to 3, according to the embodiments of the invention, may be implemented using hardware and/or software means, for example using a microcontroller or digital signal processor or any other multi-purpose integrated circuit comprising instruction processing capability, interface circuitry and memory.

The effect of the automatic normalization of physiological signals, according to an embodiment of the invention, is shown in FIG. 4. In FIG. 4 the Galvanic Skin Response (GSR) of two subjects while performing a series of activities is shown. On the right plot the proposed normalization has been applied, showing significant reductions in GSR differences between two subjects for the recorded activities.

The reduction in Root Mean Square Error (RMSE) can be seen in FIG. 5, for different activities of the subjects. In FIG. 5 we show the results of a possible application of the proposed method (energy expenditure estimation), implemented on two devices: an ECG Necklace and a Wristband. The energy expenditure estimation error is reported without using physiological signals (showing the highest errors), when using physiological signals (showing that physiological signals are important for more accurate prediction) and when using normalized physiological signals, showing that error reduction can be further increased by the proposed approach.

The invention claimed is:

1. A device comprising:
   a data input module configured to receive information about a living being's physiological signals, coordinates, and motion intensity;
   an activity recognition module configured to calculate, from information received about the living being's motion intensity, activity of the living being;
   a location recognition module, configured to calculate, from information received about the living being's coordinates, a location of the living being;
   a memory storage configured to store information about the living being's physiological signals and the activity of the living being in association with the location of the living being;
   a normalization parameters estimator module configured to calculate, from a plurality of physiological signal values associated with calculated activities and calculated locations, statistics of a distribution of the physiological signal values for each activity or a subset of activities in each location, and use a mathematical model to calculate a plurality of normalization parameters for each location; and
   a model selector module configured to determine, based on the plurality of normalization parameters and the living being's location, a set of location-specific normalization parameters used to further calculate normalized physiological signals for the living being, wherein the model selector module is further configured to calculate the normalized physiological signals for the living being by applying the location-specific normalization parameters to the physiological signals, depending on the living being's location, and wherein the normalized physiological signals for the living being include information about one or more of heart rate, galvanic skin response, skin temperature, skin humidity, or respiration.

2. The device of claim 1, wherein the activity recognition module is configured to determine at least a rest activity and a moving activity of the living being.

3. The device of claim 2, wherein the moving activity is associated with at least a first motion intensity, and wherein the normalization parameters estimator module is configured to calculate, for each location, a first physiological signal values summary based on a distribution of physiological signal values associated with the first motion intensity and a second physiological signal values summary based on a distribution of physiological signal values associated with the rest activity.

4. The device of claim 1, wherein the location recognition module is configured to determine at least two different locations.

5. The device of claim 1, wherein the normalization parameters estimator module uses a mathematical model based on information about physiological signal values distribution, activity, and location.

6. The device of claim 5, wherein the mathematical model expresses a relation between a plurality of physiological signal values associated with each calculated activity and location and a baseline and range of physiological signal values for the living being.

7. The device of claim 6, wherein the mathematical model further considers information about anthropometric characteristics of the living being.

8. The device of claim 1, further comprising an application module configured to calculate, from the living being's normalized physiological signals, an additional application-specific parameter associated with the living being.

9. The device of claim 8, wherein the application module is further configured to use information about the living being's motion intensity, the livng being's coordinates, and/or anthropometric characteristics of the living being for calculating the additional application-specific parameter.

10. The device of claim 9, wherein the additional application-specific parameter associated with the living being is an energy expenditure value or a stress level.

11. A system comprising:
  a device, the device comprising:
    a data input module configured to receive information about a living being's physiological signals, coordinates, and motion intensity;
    an activity recognition module configured to calculate, from information received about the living being's motion intensity, activity of the living being;
    a location recognition module, configured to calculate, from information received about the living being's coordinates, a location of the living being;
    a memory storage configured to store information about the living being's physiological signals and the activity of the living being in association with the location of the living being;
    a normalization parameters estimator module configured to calculate, from a plurality of physiological signal values associated with calculated activities and calculated locations, statistics of a distribution of the physiological signal values for each activity or a subset of activities in each location, and use a mathematical model to calculate a plurality of normalization parameters for each location; and
    a model selector module configured to determine, based on the plurality of normalization parameters and the living being's location, a set of location-specific normalization parameters used to further calculate normalized physiological signals for the living being, wherein the model selector module is further configured to calculate the normalized physiological signals for the living being by applying the location-specific normalization parameters to the physiological signals, depending on the living being's location, and wherein the normalized physiological signals for the living being include information about one or more of heart rate, galvanic skin response, skin temperature, skin humidity, or respiration.

12. The system of claim 11, wherein the device further comprises an application module configured to calculate, from the living being's normalized physiological signals, an additional application-specific parameter associated with the living being.

13. The system of claim 12, wherein the additional application-specific parameter associated with the living being is an energy expenditure value or a stress level.

14. A method for calculating normalized physiological signals of a living being, the method comprising:
  receiving information about physiological signals, motion intensity, and coordinates of the living being;
  detecting activity of the living being from information received about the living being's motion intensity and storing information about the living being's physiological signals and the motion intensity in association with the detected activity;
  detecting a location of the living being from information received about the living being's coordinates and storing information about the living being's physiological signals and the coordinates in association with the detected activity and location;
  determining, from a plurality of physiological signal values associated with a plurality of activities and locations, statistics of a distribution of physiological signal values for each activity or a subset of activities and in each location;
  calculating, using the statistics of the distribution of physiological signal values, a baseline and range of the physiological signals for the location of the living being; and
  normalizing, using the baseline and range of the physiological signals and depending on the living being's location, the living being's physiological signals, wherein the normalized physiological signals include information about one or more of heart rate, galvanic skin response, skin temperature, skin humidity, or respiration.

15. The method of claim 14, further comprising calculating, from the living being's normalized physiological signals, an additional application-specific parameter associated with the living being.

16. The method of claim 15, wherein the additional application-specific parameter associated with the living being is an energy expenditure value or a stress level.

* * * * *